(12) United States Patent
Loyd et al.

(10) Patent No.: US 7,422,105 B2
(45) Date of Patent: Sep. 9, 2008

(54) PACKAGED TAMPON AND APPLICATOR ASSEMBLY

(75) Inventors: Adrienne Rae Loyd, Neenah, WI (US); Joseph DiPalma, Neenah, WI (US); Thomas William VanDenBogart, Slinger, WI (US); Marcus David Weiher, Sherwood, WI (US); Lynn Marie Matheus, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 187 days.

(21) Appl. No.: 11/322,817

(22) Filed: Dec. 30, 2005

(65) Prior Publication Data

US 2007/0151885 A1 Jul. 5, 2007

(51) Int. Cl.
*A61B 19/02* (2006.01)
*B65D 33/00* (2006.01)

(52) U.S. Cl. .................. 206/438; 206/440; 206/484; 206/815; 383/35

(58) Field of Classification Search ......... 206/438–441, 206/484–484.2, 815; 383/35; 602/79; 604/385.02
See application file for complete search history.

(56) References Cited

U.S. PATENT DOCUMENTS

| | | | | |
|---|---|---|---|---|
| 2,329,360 A | * | 9/1943 | Salfisberg | 206/484 |
| 2,565,336 A | * | 8/1951 | Adler | 206/484 |
| 3,092,251 A | * | 6/1963 | Jaggers | 206/438 |
| 3,123,210 A | * | 3/1964 | Hermanson et al. | 206/439 |
| 3,189,702 A | * | 6/1965 | Wall et al. | 206/440 |
| 3,233,821 A | * | 2/1966 | Ehlers | 383/35 |
| 3,604,616 A | * | 9/1971 | Greif | 206/439 |
| 5,133,457 A | | 7/1992 | Kadel | |
| 5,352,466 A | * | 10/1994 | Delonis | 383/35 |
| 5,462,166 A | | 10/1995 | Minton et al. | |
| 6,131,736 A | * | 10/2000 | Farris et al. | 206/440 |
| 6,309,104 B1 | * | 10/2001 | Koch et al. | 206/484 |
| 6,568,533 B1 | * | 5/2003 | Tanaka et al. | 206/484 |
| 6,994,696 B2 | * | 2/2006 | Suga | 604/385.02 |
| 7,073,666 B2 | * | 7/2006 | Arndt | 206/440 |
| 7,101,358 B2 | * | 9/2006 | Domeier et al. | 604/385.02 |
| 2003/0220625 A1 | | 11/2003 | Domeier et al. | |
| 2004/0112779 A1 | | 6/2004 | Arndt | |

FOREIGN PATENT DOCUMENTS

WO WO 03/099184 A1 12/2003

* cited by examiner

*Primary Examiner*—Bryon P Gehman
(74) *Attorney, Agent, or Firm*—Ralph H. Dean, Jr.; Sebastian C. Pugliese, III

(57) ABSTRACT

An easy open package for personal care products which has sensory cues as to the location of the opening of a wrapper component. In addition, the present invention provides a wrapper component which has a gradient seal which allows the user to effectively open the wrapper without unnecessarily tearing the wrapper.

16 Claims, 8 Drawing Sheets

PACKAGED TAMPON AND APPLICATOR ASSEMBLY

BACKGROUND OF THE INVENTION

The present invention relates generally to an easy open wrapper for absorbent personal care products, in particular for a tampon and applicator.

Vaginal tampons are disposable absorbent articles sized and shaped (e.g., cylindrical) for insertion into a woman's vagina for absorption of body fluids generally discharged during the woman's menstrual period. Insertion of the tampon into the vagina is commonly achieved using a tampon applicator that comes initially assembled with the tampon. The applicator, which is often made of plastic or cardboard, is disposable. Thus, after the applicator has been used to insert the tampon into the user's vagina the applicator is discarded.

Typically, a single tampon and applicator assembly are packaged together as an individual unit in a disposable wrapper to maintain both the tampon and the applicator in a hygienic condition. Thus, before the tampon and applicator assembly can be used, it must be removed from the wrapper. Conventionally, tampon wrappers are provided with a serrated edge, e.g., having numerous peaks and valleys. The valleys of the serrated edge provide multiple tearing points for use in tearing open the wrapper. One drawback to this approach is that it often leads to small pieces of the wrapper being separated from the wrapper at the serrated edge. As a result, the user must often make multiple tears in order to open the wrapper sufficiently to remove the tampon and applicator assembly, which is frustrating to the user and creates small pieces of wrapper that are difficult to manage (i.e., inconvenient to pick up and throw away).

Another known wrapper construction provides a tear strip in the wrapper, typically extending the length of the wrapper. A tab may be attached to the tear strip at its edge so that it can be grasped by the user. In use, a woman grasps the tab and pulls the tab in the direction of the tear strip thereby creating an opening in the wrapper through which the tampon and applicator assembly is removed. The tear strip may also be engaged by tearing a serrated edge in the absence of a tab. Often, the tear strip extends the length of the wrapper. Thus, tearing the tear strip from the wrapper completely tears open the wrapper along its length. As a result, the tampon applicator and wrapper are commonly disposed of separately. Moreover, the tabs can sometimes be difficult to locate and grasp, making it difficult to open this type of wrapper.

Another known applicator and tampon wrapper construction has a pair of opening members (tabs) attached along a rupturable seal along one of the edges of the wrapper. The rupturable seal lines are designed to separate when the opening members are forced in opposite directions. The rupturable seal lines are adjacent permanent seal lines which are designed to stop the opening of the wrapper at the end of the rupturable seal lines. These tabs assist the user in opening the wrapper; however these tabs can be difficult to locate and grasp, making it difficult to open the wrapper. In addition, the permanent seals act as a hard stop for the opening of the wrapper. As the rupturable seal meets the permanent seal, the opening of the wrapper comes to an abrupt stop, which can result in tearing of the wrapper, or ejecting the unused applicator and tampon combination from the wrapper. When the wrapper tears, it makes it difficult to place a used applicator into the wrapper for hygienic disposal. When the unused applicator and tampon combination is ejected from the wrapper, it will often become non-hygienic making it unsuitable for use.

There is a need, therefore, for a packaged tampon and applicator assembly that facilitates opening of the wrapper while maintaining the ability of the wrapper to be subsequently used to hygienically wrap and discard the used tampon applicator.

SUMMARY OF THE INVENTION

In the one embodiment of the present invention, provided is a packaged absorbent personal care product. The package contains a personal care product and a wrapper component. The wrapper component has a front panel and a back panel, each panel having a first longitudinal end, a second longitudinal end, a first side edge and a second side edge. The front panel is joined to the back panel at or near each of the longitudinal ends and each of the side edges in a manner to create an interior space adapted to receive and sealingly enclose the personal care product. Further, the wrapper has an opening device located at the first longitudinal end or along on the first side edge, wherein the opening device has a first tab and a second tab. The first tab extends from the front panel and the second tab extends from the second panel. The wrapper component is provided with a sensory cue to distinguish the tabs of the opening device from the front and back panels of the wrapper in which the tabs extend, or to distinguish the first tab from the second tab. In this embodiment of the present invention, the sensory cue may also provide indicia to the user of the absorbent personal care product as to the location of the opening device for the wrapper, thereby directing a users attention to the opening device and assisting the user in opening the wrapper.

In another embodiment of the present invention, provided is a packaged absorbent personal care product having an absorbent personal care product; and a wrapper. The wrapper has a front panel and a back panel, each panel having a first longitudinal end, a second longitudinal end, a first side edge and a second side edge. The front panel is joined to the back panel by at least one longitudinal seal and at least one lateral seal in a manner to create an interior space adapted to receive and sealingly enclose the personal care product. The lateral seal is located along a line which is essentially parallel with the first longitudinal end and the longitudinal seal has a beginning located at or near the lateral seal and an ending located at or near the second longitudinal end. The longitudinal seal is located along a line which is essentially parallel with the first side edge and the longitudinal seal has a gradient seal strength which increases from the beginning of the longitudinal seal towards the end of the longitudinal seal. The gradient seal strength allows a user to open the wrapper and provide a slow but effective stop for the opening process. The wrapper component also provided with at least one additional seal, which may be a lateral seal or a longitudinal seal. In a further aspect of this embodiment of the present invention, the additional seal is a longitudinal seal and the additional longitudinal seal also has a gradient seal strength.

In an additional embodiment of the present invention, the two embodiments described above may be combined to provide a wrapper having a gradient seal strength and an easy to find opening device.

DEFINITIONS

Figure 1:
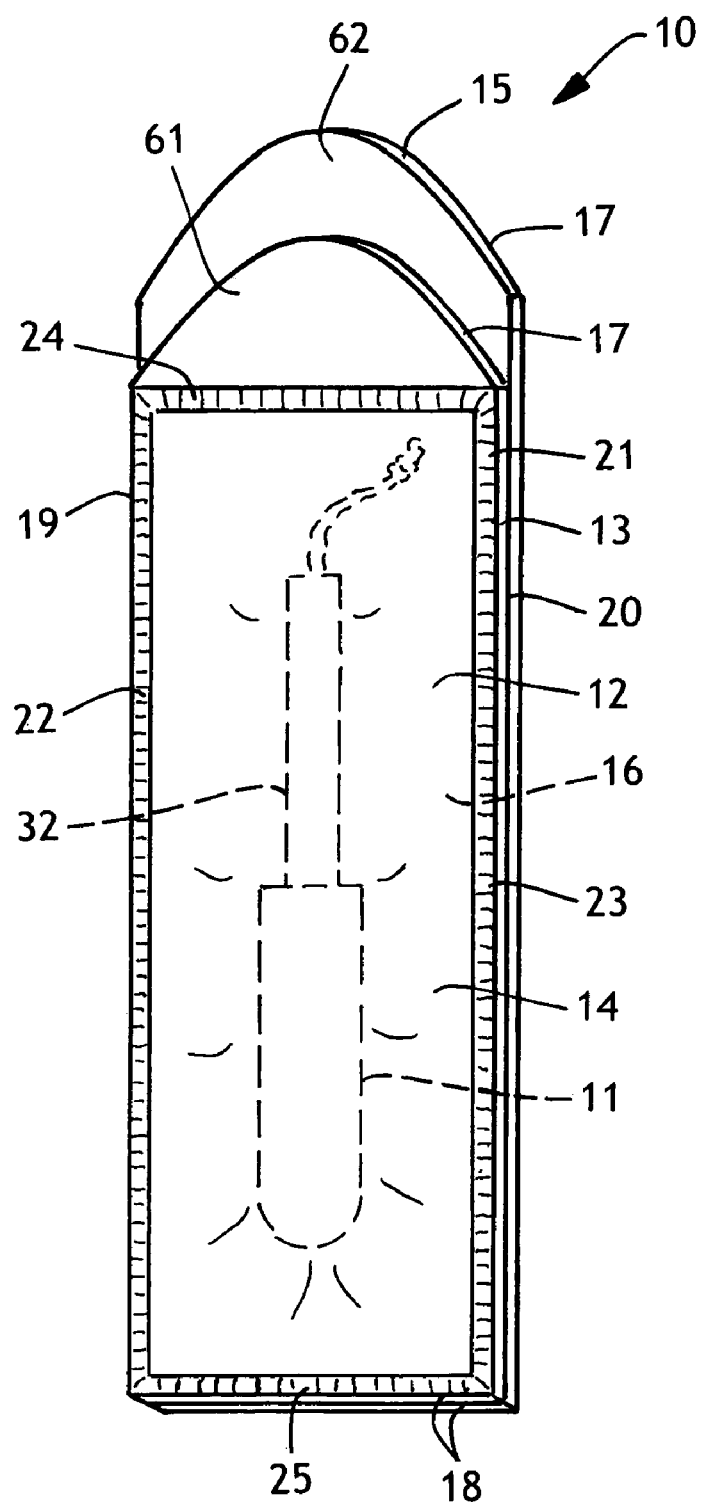
FIG. 1 shows a perspective view of one embodiment of the present invention having a wrapper with an opening device on one of the longitudinal ends of the wrapper and a personal care product contained within the wrapper.

It should be noted that, when employed in the present disclosure and claims, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "sensory attribute" means a physical feature of the front panel, back panel or one or both of the tabs of the opening device of the wrapper component which may be perceived by a user. Physical features include, for example, color, texture, shape, a graphic, text, alpha-numeric characters, and/or a pattern, or other similar physical features.

As used herein, the term "sensory cue" is intended to mean information provided to a user of the products within the wrapper which distinguishes the front or back panels of the wrapper component from the first tab and second tab of the opening device, or to distinguish the first tab from the second tab of the opening device. A sensory cue is provided to the user of the product by having different sensory attributes on the tabs of the wrapper which provides a user clear indicia as to the location of the tabs in relationship to the wrapper and where the wrapper may be opened. Alternatively, a sensory cue provides a user of the packaged absorbent personal care article clear indicia to distinguish the first tab from the second tab of the opening device.

As used herein, "clear indicia" means that at a first encounter with the wrapper, a user can easily ascertain the location of the opening device and tabs. Stated another way, the difference in the sensory attributes of the tabs in relation to each other or in relationship to the wrapper is such that the tabs of the opening device are clearly apparent to a user of the packaged absorbent personal care product, which easily draws the user's attention to the opening device.

It should be understood that the term "personal care article" as used herein refers to any article used to control bodily fluids, and includes "absorbent products," which refers to any article configured to absorb and retain bodily exudates, including urine, bowel movements, blood and menses, and includes such a product in a packaged and unpackaged configuration. As such, personal care products, as used herein, includes without limitation, diapers, child toilet training pants, adult incontinence garments, male incontinence products, tampons, vaginal suppositories, panty liners, pads, sanitary napkins, tissues, wipes, etc. Examples of commercially available personal care products include, without limitation, Poise® feminine care products, including pantiliners and pads, and Kotex® feminine care products, including pads, tampons and liners, Depend® undergarments, underwear and guards, all available from Kimberly-Clark Corporation, Neenah, Wis.

DETAILED DESCRIPTION OF THE INVENTION

Figure 2:
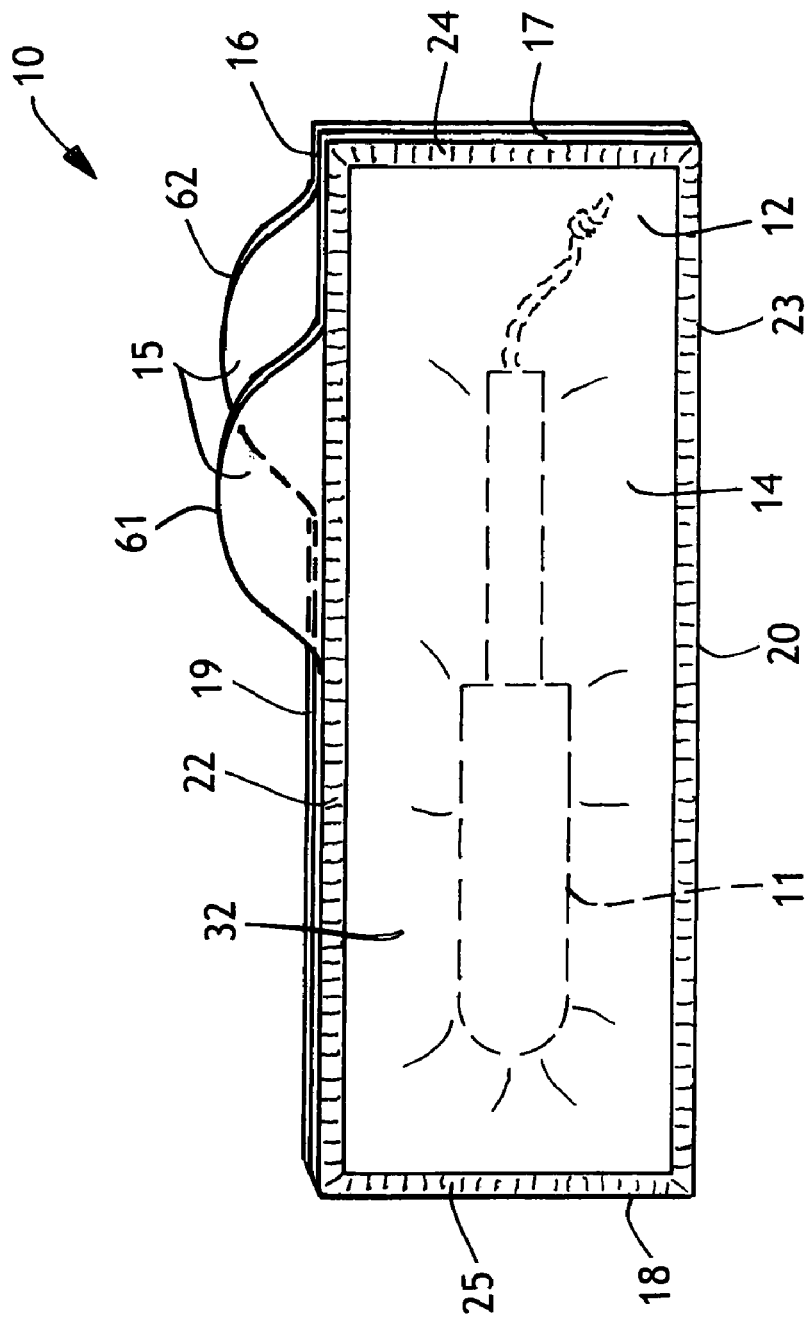
FIG. 2 shows a perspective view of one embodiment of the present invention having a wrapper with an opening device on one of the side edges of the wrapper and a personal care product contained within the wrapper.

Referring to the drawings and in particular to FIGS. 1 and 2, shown is a wrapper component 12 having an absorbent personal care product 11 contained within the wrapper component 12, forming a packaged absorbent personal care product 10.

The wrapper of the present invention has a front panel 14 and a back panel 16, each panel having a first longitudinal end 17, a second longitudinal end 18, a first side edge 19 and a second side edge 20. The front panel 14 is joined to the back panel 16 along each of the longitudinal ends 17, 18 and each of the side edges 19, 20 in a manner to create an interior space 13 adapted to receive and sealingly enclose the absorbent personal care product 11. To assist or facilitate opening the wrapper 12 to access the interior space 13 of the wrapper 12 and the absorbent personal care article 11 contained therein, the wrapper 12 further has an opening device 15 located at the first longitudinal end 17 as is shown in FIG. 1 or along on the first side edge 19 as is shown in FIG. 2. Thus, the wrapped personal care article 10 can be carried as a single unit by the user (e.g., in a purse, backpack, or a pocket) in a sealed, hygienic condition.

It is noted that the first longitudinal end 17 and the first side edge 19 are selected for description of the opening device 15 and are not intended to be limited thereto. That is, the second longitudinal end 18 or the second side edge 20 may contain the opening device 15, but for description herein, the longitudinal end or the side edge having the opening device will be referred to as the first longitudinal edge 17 or the first side edge 19, whichever the case may be.

In the present invention, a variety of materials may be used to prepare the wrapper 12 component of the packaged absorbent personal care product 10. Generally, it is desirable that the materials used to prepare the wrapper 12 are flexible and fluid impermeable and have a sheet-like appearance. When impermeable materials are used, the wrapper 12 may be effectively used to dispose of a used absorbent personal care article or in the case of tampons, a used tampon applicator. Exemplary materials include thermoplastic films, nonwoven webs, paper, and laminates of one or more of these materials. The materials should be strong enough to resist tearing prior to use which may compromise the hygienic conditions of the absorbent personal care product 11 contained within the package 10. It is also desirable to use a material which emits a low level of noise when the wrapper is being opened to provide discretion to the user. Ideally, the wrapper component will not emit, or will emit at a very low level, a rattling, crinkling and/or scratching sound during use, in particular during opening of the wrapper 12. One example of a material which can be used is a polyolefin film having a thickness of about 0.013 mm (about 0.5 mil) to about 0.13 mm (about 5 mils).

To form wrapper component 12 of the present invention, a single piece of material may be used or two pieces of material may be used. In the case where a single piece of material is used, the material may be folded along the second longitudinal end 18 or along the second side edge 20. When folded, one portion of the material forms the front panel 14 and another portion forms the back panel 16. In either case, when a single piece of material is used, the wrapper 12 may be effectively sealed by sealing the material along at or near three of the four edges or ends. For example, when the second side edge 20 is a fold line of the sheet material, the wrapper 12 may be sealed by sealing at or near the two longitudinal ends 17, 18 and the first side edge 19. When the second longitudinal end 18 is a fold line of the single piece of material, the wrapper component 12 may be sealed by sealing at or near the two side edges 19, 20 and the first longitudinal end 17. This does not mean that the wrapper cannot be sealed at or near the folded edge or end, the wrapper may be sealed at or near the folded edge or end; however, it is not necessary to do so to hygienically seal the absorbent personal care product 11 within the wrapper 12. In addition, the front and back panels 14, 16 of the wrapper 12 may be prepared from two pieces of materials which are joined together. When two pieces are used to form the front and back panels 14, 16, it is required that the front and back panels of the wrapper be joined together at or near each of the first and second longitudinal ends 17, 18 and the first and second side edges 19, 20, to form a hygienic seal.

As is shown in FIGS. 1 and 2, the wrapper of the present invention also has a seal 21 which extends around the wrapper near ends and side edges of the wrapper. The seal 21 effectively joins the front panel 14 to the back panel 16 of the wrapper. The seal 21 as shown has a first lateral seal 24 located near the first longitudinal end 17; a second lateral seal 25 located at or near the second longitudinal end 18; a first longitudinal seal 22 located at or near the first side edge 19; and a second longitudinal seal 23 located at or near the second side edge 20. As is stated above, each of the seals may be used to join the front panel 14 to the back panel 16 of the wrapper component 12 and all four seals are needed if the wrapper 12 is prepared from two pieces of material. If the wrapper is prepared from a single piece of material, then only three of the four seals are needed to join the front panel 14 to the back panel 16.

The seals 21 can be prepared using any method known to those skilled in the art, including heat sealing, ultrasonic sealing, adhesive sealing, crimping or embossing with heat or pressure, and a combination thereof. The seals join the front panel 14 of the wrapper to the back panel 16 and create an interior space within the wrapper 12 to hold the absorbent personal care article 11. The seals also desirably create a wrapper 12 having an interior space 13 which is hygienic. In addition, the seals are designed to be ruptured by the user of the absorbent personal care products to access the absorbent personal care products 11 within the wrapper 12. By "ruptured" it is meant that a user can open the wrapper by breaking the seal. In one embodiment of the present invention, the seal 21 may be heat embossed seal lines, which will release when pulled apart in opposite directions. Embossed seal lines may provide a degree of aesthetic appeal to the wrapper, by creating a seal 21 which has a pleasing pattern.

In another embodiment of the present invention, the seal lines 21 may be adhesive seal lines. Adhesive seal lines provide an additional advantage. In particular, when adhesive seal lines are used, the wrapper 12 may be resealed after use along the adhesive seal lines. This provides the advantage that a used personal care product 11 may be placed into the wrapper after use for disposal. Suitable adhesives included pressure sensitive adhesives. In one embodiment of the present invention, a combination of embossed seals and adhesive seals may be used to provide an aesthetically pleasing wrapper which is resealable.

Figure 3:
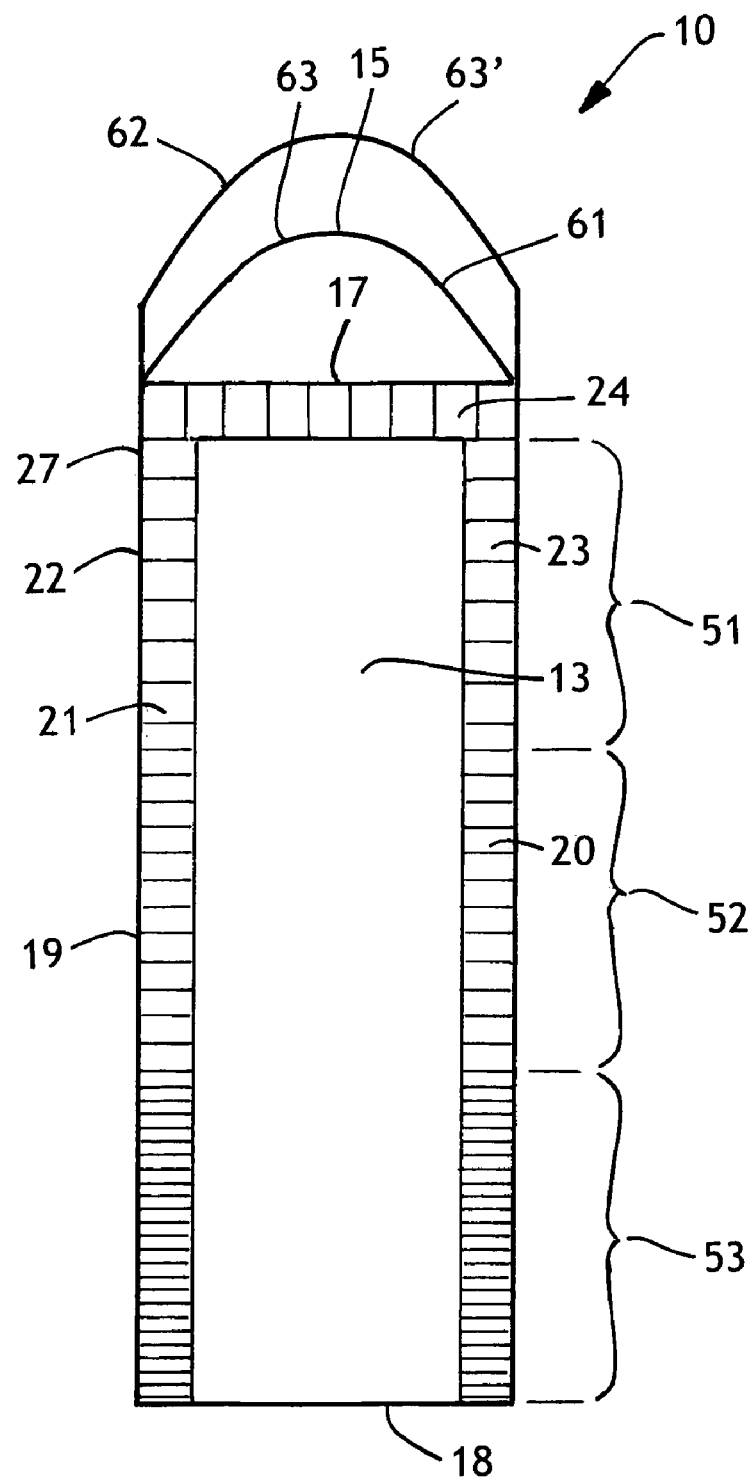
FIG. 3 shows a front view of a wrapper of the present invention with a gradient embossed seal.
Figure 4:
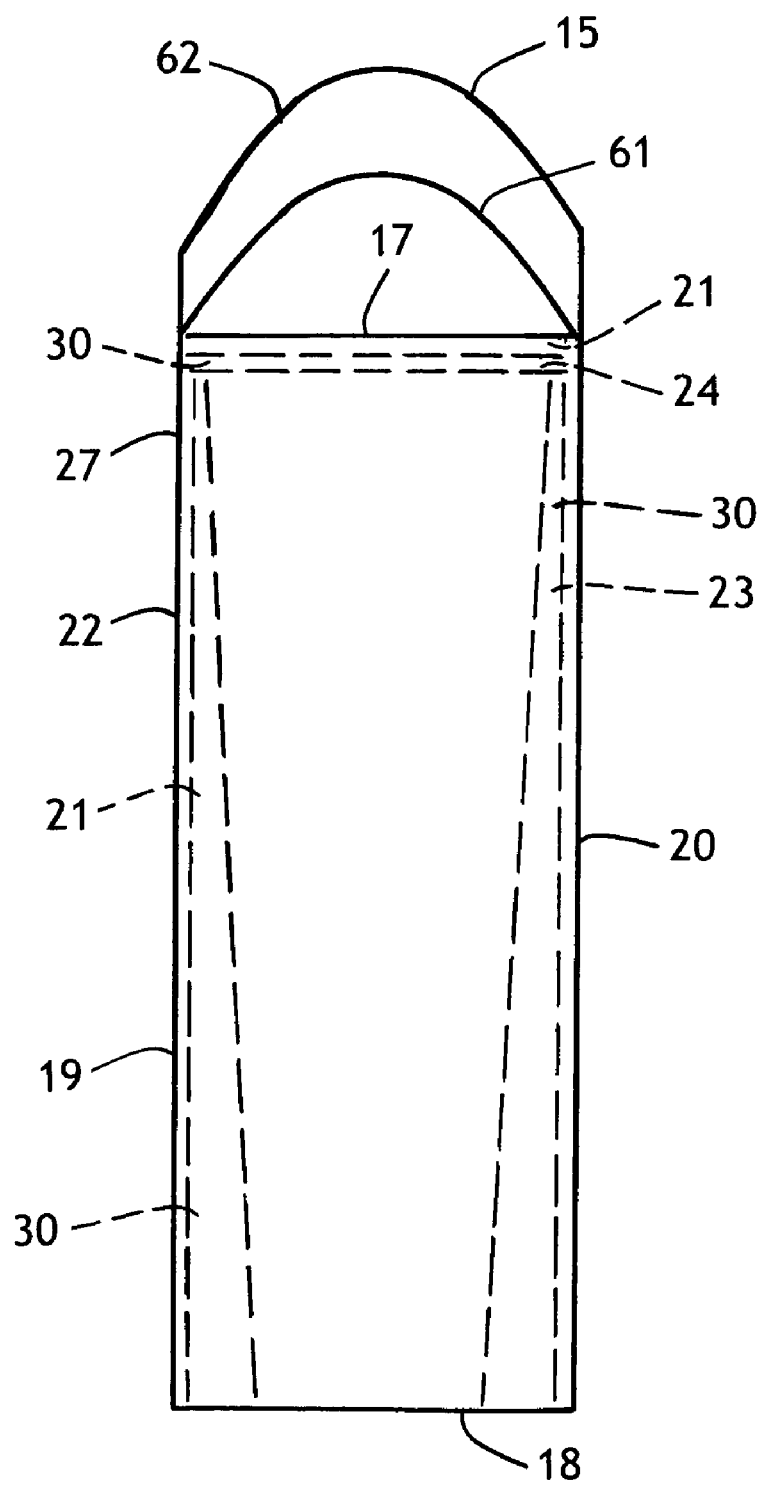
FIG. 4 shows a front view of a wrapper of the present invention with a gradient adhesive seal.

In another embodiment of the present invention, the seal lines 21 may have gradient seal strength. By "gradient seal strength", it is meant that the seal strength changes from along the length of the seal. As used herein, the phrase "the length of the seal" means the direction in which the seal 21 is the longest. To obtain a better understanding of this aspect of the present invention, attention is directed to FIGS. 3 and 4. In the case of the present invention, the seal strength of the first longitudinal seal 22 changes from the beginning 27 of the seal located at or near the lateral first lateral seal 24 and increases in strength as the seal gets closer to the second longitudinal end. In FIG. 3, the seals are shown as embossed heat seals which increase in peel strength as the seal gets closer to the second longitudinal end. In the case of FIG. 3, the weaker seal portions have a smaller bond area than the stronger portions of the seal. It is known in the art that larger bond areas in heat seals have higher seal strength than bond areas having a smaller area. As is shown in FIG. 3, the bond area near the first longitudinal seal 22 at or near the first lateral seal 24 has a smaller bond area than the longitudinal seal near the second longitudinal end 18. As a result, the first longitudinal seal 22 has higher seal strength near the second longitudinal end 18 as compared to the seal strength of the first longitudinal seal 22 near the first lateral seal 24. In FIG. 4, the gradient seal is formed by using an adhesive 30. As is shown in FIG. 4, the adhesive 30 is applied wider near the second longitudinal end 18 as compared to the beginning 27 of the first longitudinal seal 22. As a result, the seal strength (peel strength) of the first longitudinal seal line 22 increases as the first longitudinal seal line 22 approaches the second longitudinal end 18. These described methods are intended to only be exemplary and other methods to form a gradient seal may be used without departing form the present invention. Other examples of creating a gradient seal include, for example, varying the particular adhesive used along the seal line such that a more aggressive (higher shear strength) is used as the seal line approaches the second longitudinal end 18; using a higher basis weight of the adhesive near the second longitudinal end 18 as compared to the beginning 27 of the seal line; applying a release agent to one or both of the front and back panels in a manner that the amount of release agent is reduced as the second longitudinal end 18 is approached; or using a combination of heat seals and adhesive seals to achieve a gradient seal strength. In addition, combinations of these methods may also be used as well as other methods known to those skilled in the art for preparing a gradient seal.

In the present invention, one or both of the longitudinal seals 22 and 23, if present, may have a gradient seal. In addition, one or both of the lateral seals 24 and 25 may also have a gradient seal strength. However, if the opening device described above is located on the first side edge 19, then only the first longitudinal seal needs to have the gradient seal strength. If the opening device is located on the first longitudinal end 17, then it is desirable that both the first and second longitudinal seals 22 and 23 have a gradient seal strength, if a gradient seal strength is desired. Generally, it is not required that the first and second lateral seals 24, 25 have a gradient seal strength, although it is not outside the present invention if one or both of the lateral seals 24, 25 have a gradient seal strength.

The gradient seal strength of the present invention may be provided in a variety of ways. One way is to provide a series of seals adjacent one another such that each seal in the series of seals starting from the beginning 27 near the first lateral seal has a peel strength which is greater than the previous seal. Alternatively, the gradient seal may be formed in a continuous fashion, where the seal gradually increases in strength from the beginning of the seal to the end near the second longitudinal end. When the gradient seal is a series of seal sections adjacent one another, then there are greater than three seal sections in the series. Typically, depending on factors such as the length of the longitudinal edges and the degree of change desired between each of the seal sections in the series of seal sections, there may be between 3 and 10 adjacent seal sections in the series. For example, as is shown in FIG. 3, the first section of seals 51 has a seal strength which is less than the second section of seals 52. In addition, the second section of seals 52 has a seal strength which is less than the third section of seals 53. As a result, a gradient seal strength is achieved, where the seal strength changes in the direction of the longitudinal seals 22 and 23.

In the present invention, the absorbent personal care products 11 of the present invention are placed into a wrapper 12 having an opening feature or opening device 15. The opening device of the present invention has a first tab 61, which is attached to the front panel 14 and a second tab 62, which is attached to the back panel 16, as is shown in FIGS. 1, 2, 3, and 4. The first tab 61 may be the same size as the second tab 62, as is shown in FIG. 2, or one of the tabs may be larger than the other tab, as is shown in FIGS. 1, 3 and 4. For purposes of discussion herein, the second tab 62 which be discussed as being the larger tab, when there is a difference in the size of the tabs. It is also pointed out that the terms "front panel" and "back panel" are relative terms, but for the purposes of discussion herein, the back panel will be the panel with a larger tab.

In the present invention, the opening feature 15 is highlighted to the user of the absorbent personal care products by providing a sensory cue to the user. A sensory cue within the scope of the present invention may be any sensory cue which will provide an indication to the user of the absorbent article where the tabs of the opening device are located on the wrapper of the present invention. The sensory cue can be a visual cue, a tactile cue, an audible cue, an olfactory cue, a cue which invokes the sense of taste or a combination of one or more of these cues. From a practical standpoint, visual or tactile cues are desirable. This sensory cue aids the user of the absorbent article to locate the place on the wrapper component in which the wrapper component may be opened to access the absorbent article contained within the wrapper.

From a practical standpoint, the visual or tactile cues are desirable. However, this does not mean that other sensory cues are intended to be excluded from the present invention. For example, audible cues, olfactory cues and cues which invoke taste can be very useful for users of the products who are severely visually impaired to the point that they are blind or essentially blind. In the case of taste, a flavoring could be placed on one or both tabs 61, 62 of the opening device panel near the free ends 63 of the tabs to allow a user to use the sense of taste to find the opening for the wrapper. Likewise, a "scratch and sniff" type coating could be placed on or near one the tabs of the wrapper to allow a user to use the sense of smell to locate the opening. In a similar manner, the audible means could be used in the present invention by changing the type of material or thickness of the material used for the tabs so that when touched or handled, the sound generated by the flap or second panel is different from the remainder of the pouch material.

In the present invention, the sensory cue is provided by a contrast between the front and back panels 14, 16 of the wrapper as compared to the tabs 61, 62 of the opening device 15. This may be accomplished by providing the front and back panels 14, 16 with a first set of sensory attributes and the tabs 61, 62 of the opening device with a second set of sensory attributes. At least one attribute of the first set of sensory attributes or the second set of sensory attributes is different from the other sensory attributes of the other set of sensory attributes. In the present invention, the difference in sensory attributes on the front and back panels 14, 16 compared to the tabs 61, 62 of the opening device must provide clear indicia as to where the opening device is located at a first encounter with the wrapper component 12. That is, the user should not have to think about the location of the opening device 15 based on the sensory attributes on the tabs 61, 62 of the opening device 15 or the sensory attributes present on the front and back panels 14, 16.

Sensory attributes can take many forms and can include, for example, one or more colors, textures, shapes, graphics, text, alpha-numeric characters, and/or patterns, including indicia formed by dying, printing and/or embossing, or by otherwise altering the relative texture of the second panel relative to the first panel. Other examples include making the tabs 61, 62 of the opening device from a different material than the front and back panels 14, 16, having the tabs 61, 62 be a different color from the front and back panels 14, 16; placing patterns either by embossing or printing onto the tabs 61, 62 of the opening device which are different from patterns on the front and back panels 14, 16; having the tabs 61, 62 of the opening device shaped along the free edge 63 of the individual tabs; or any other attribute differences between the tabs of the opening device and the front and back panels which may allow a user to ascertain the location of the opening device as compared to the front and back panels by the contrast created by the difference in at least one attribute of the opening device and the front and back panels.

In another embodiment of the present invention, the tab 61 associated with the front panel 14 and the tab 62 associated with the back panel 16 may also be provided with separate sensory cues which distinguish the front tab 61 from the back tab 62. Any of the above described methods may also be applied to the tabs to provide a sensory cue.

Figure 5A:
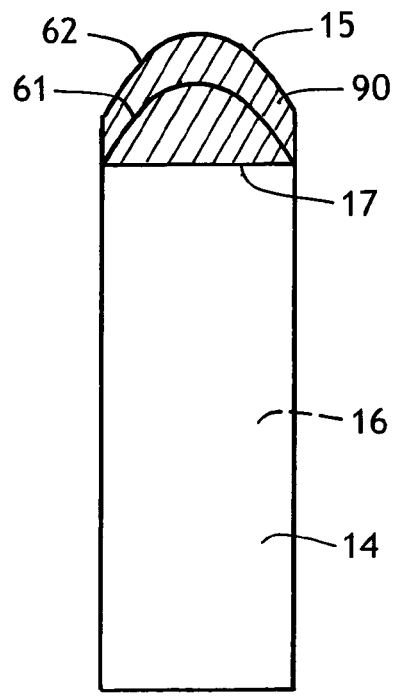
FIGS. 5A-5G show possible configurations of the sensory cue provided by the present invention.

To gain a better understanding of the sensory cue provided by the present invention, attention is directed to FIGS. 5A-5G. In each of FIGS. 5A-5G, at least one of the tabs 61, 62 and the front panel 14 and/or back panel 16 includes a sensory attribute 90, shown as a visual or tactile attribute. The sensory attribute 90 in FIG. 5A is present on each of the tabs 61, 62 but not on the front and back panels 14, 16. The sensory attribute 90 desirably terminates at the first longitudinal end 17 of the front and back panels 14, 16 and provides indicia as to the location of the opening device. With the sensory attribute 90 only on the tabs 61, 62, a sensory cue is provided to a user, directing the user's attention to the opening device 15. As is stated above, the sensory attributes 90 can take many forms, and can include one or more colors, textures, shapes, graphics, text, alpha-numeric characters, and/or patterns, including indicia formed by dying, printing and/or embossing, or by otherwise altering the relative texture of the tabs 61, 62, relative to the front and/or back panels. The sensory attributes 90 can further be reflective and/or glow in the dark such that the user can access the free edge in poorly lit conditions.

Figure 5B:
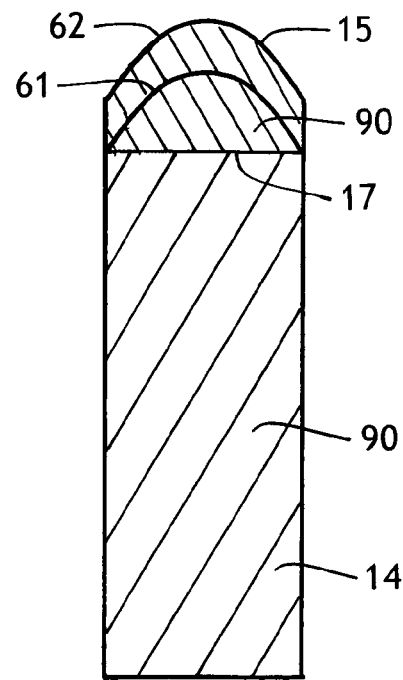

For example, in the embodiment of FIG. 5A, the sensory attribute 90 is configured as a decorative pattern applied to tabs 61, 62 of the opening device 15. In one suitable embodiment, the pattern is formed by repeating pictorials. Of course, it should be understood that the pattern can be any combination of repeating pictorials, lines, shapes, characters, etc. In the embodiment of FIG. 5B, the sensory attribute 90 is configured as a color applied to the front and back panels 14, 16 that is different than the color of the tabs 61, 62 of the opening device 15. By different color, it is meant that the colors have a hue or other color property which makes the difference visible to the casual observer. One or more colors may also be different by virtue of having a different luminosity and/or saturation/vividness. Saturation/vividness is the intensity of the color from pale to dark. The elements may also have a different gloss/finish, from a matte finish, which tends to diffuse or scatter light, to a gloss finish, which is specular.

Figure 5C:
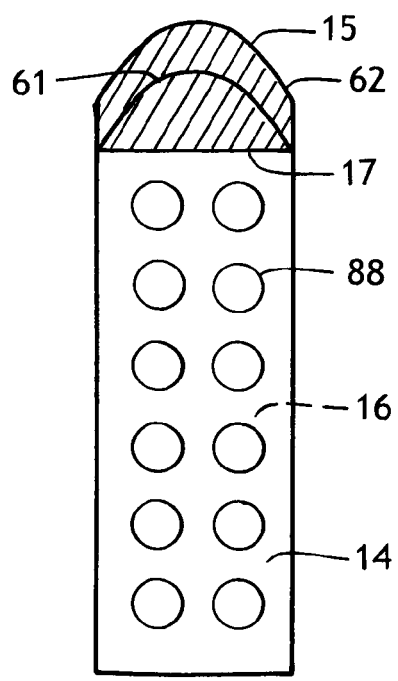
Figure 5D:
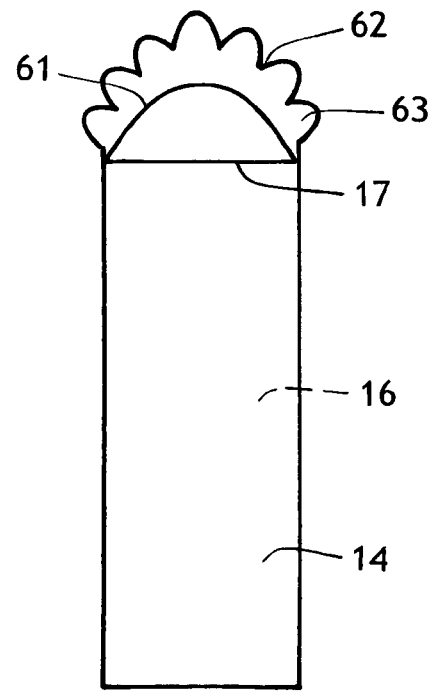
Figure 5E:
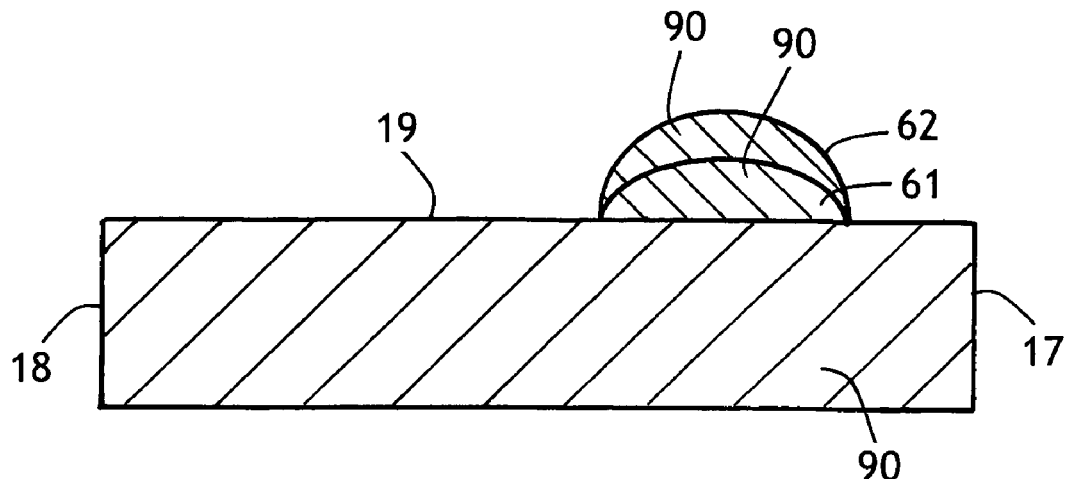
Figure 5F:
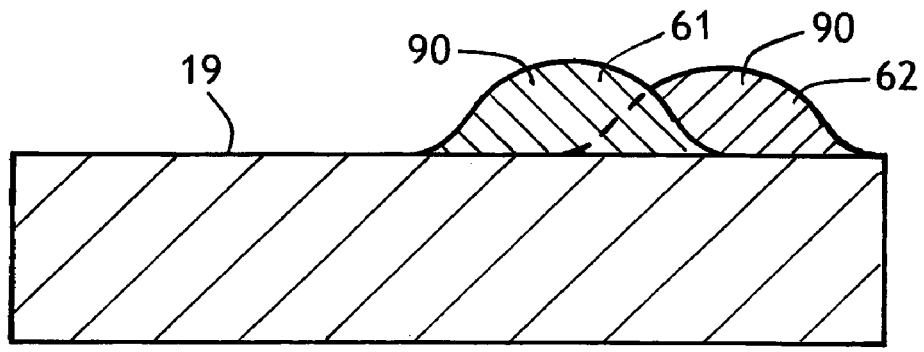
Figure 5G:
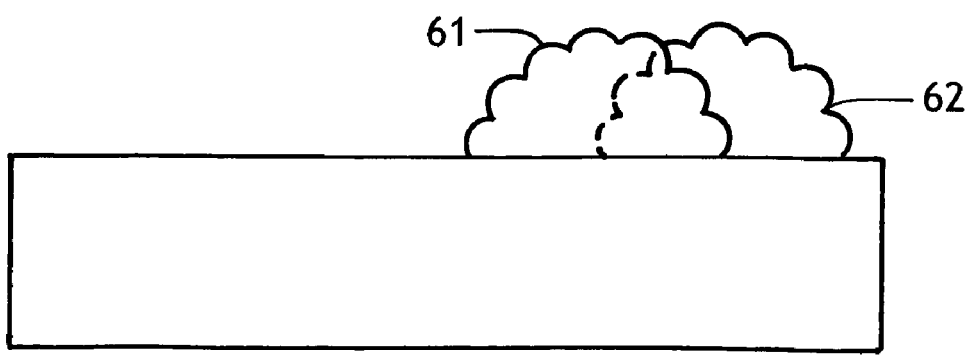

As is shown in FIG. 5C, the front and back panels 14, 16 may have a pattern 88 applied thereto which terminates at the first longitudinal end 17 of the wrapper 12 and the tabs 61, 62 of the opening device have a solid color applied thereto. In FIG. 5D, one the second tab 62 of the opening device (the back panel tab as shown) has a free end 63 with a pattern cut therein and the other tab 61 of the opening device 15 is devoid of a pattern cut free end. FIG. 5E shows a configuration of the present invention where the tabs 61, 62 of the opening device are located along the first side edge and the tabs of the opening device have a different visual cue from the front and back panels 14, 16. FIG. 5F shows a configuration of the present invention where the tabs 61, 62 of the opening device are located along the first side edge 63, with each tab 61, 62 being offset in the longitudinal direction from the other tab. In addition, as is shown in FIG. 5F, each tab has a different color or pattern thereon and the color or pattern on each tab of the opening device is different from the color or pattern on the front and back panels 14, 16 of the wrapper. FIG. 5G shows a configuration of the present invention where the tabs 61, 62 of the opening device are located along the first side edge 19 and the tabs 61, 62 of the opening device each have a free end 63 which is cut into a design. Combinations of these configurations shown in FIGS. 5A-5G may also be used without departing from the scope or spirit of the present invention.

Figure 6:
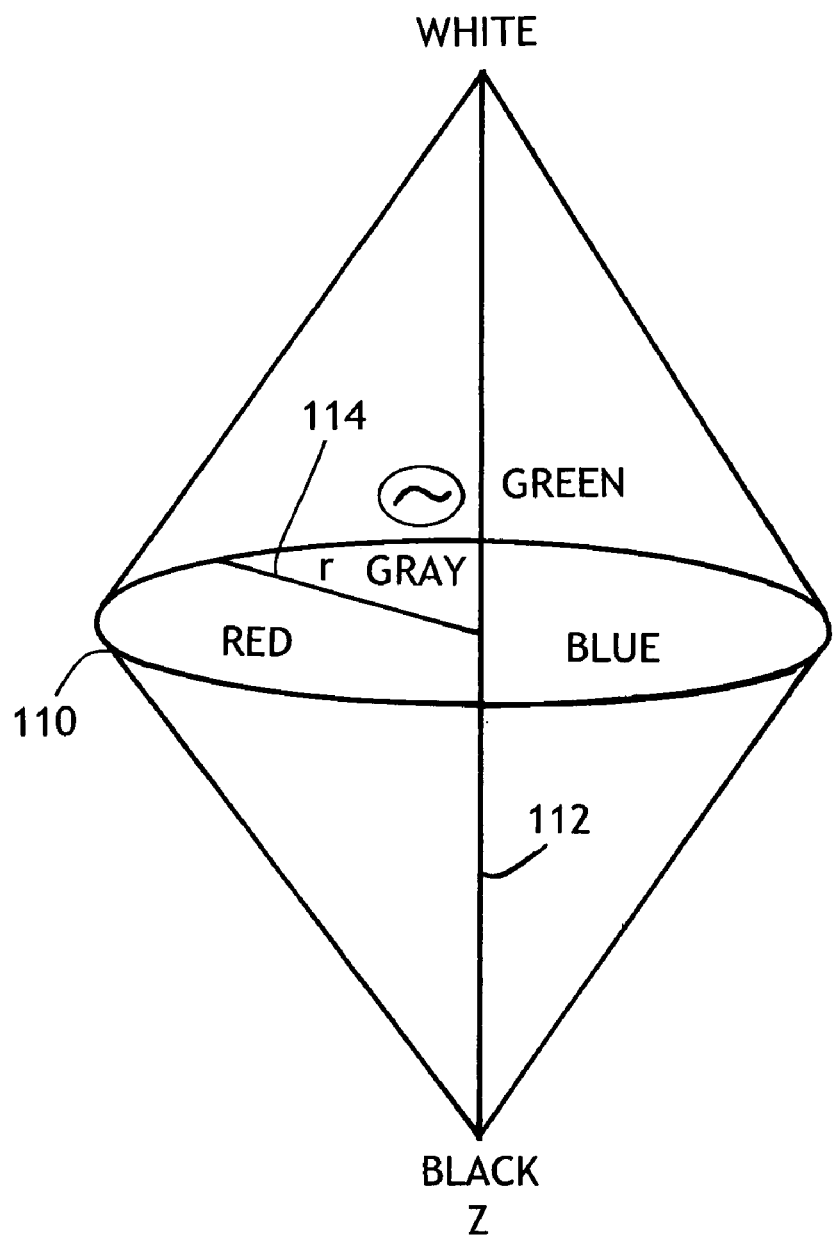
FIG. 6 is a schematic graphical illustration of hue, luminosity and saturation/vividness.

To obtain a better understanding of difference in color, attention is directed to FIG. 6, where hue is measured by the angular position around the circle 110. Two colors are considered different if they have first and second hues that are more than ±0.50 degrees from each other on the circle 110, alternatively ±5 degrees, alternatively ±30 degrees, alternatively ±90 degrees, alternatively ±150 degrees and alternatively ±175 degrees. Value (luminosity) is measured along the Z-axis 112 between white and black. Colors are considered different if they have a value difference of at least 1% of maximum (Polaroid white reference standard). Desirably, the value difference should be at least 20% of the maximum and more desirably at least 33% of the maximum. A value of one equates to white, while a value of 0 equates to black. Saturation/vividness is measured along the length of the radius (r). Colors are considered different if they have a saturation difference of at least 2.5% of maximum. Desirably, the saturation difference should be at least 7% and more desirably at least 33% of the maximum.

The hue, luminosity and saturation/vividness are measured as follows using the following-equipment calibrated in the following way.

Equipment

Quantitative calorimetric measurements are typically made using a calorimeter or spectrophotometer. However, these instruments typically have large apertures (~1 cm) requiring a large color block for meaningful determination, making them unsuitable for color determination of graphics that may be composed of narrow lines or points whose width is much less than the instrument aperture. Therefore, a Zeiss KS400 Image Analysis system was used for feature identification and calorimetric measurement.

The Zeiss KS400 used a Zeiss AxioCam color CCD camera (1300×1030 pixels, 3 channel color, 8 bit per channel) equipped with a 20 mm AF-Nikkor lens (f/2.8). The camera was mounted vertically facing down onto a sample stage and had an effective field of view of 97×80 mm. Incident sample stage illumination was by four incandescent floodlamps (Sylvania) on a double Variac (70%;90%), resulting in an illuminance of approximately 11,000 lux. The lamps were above the left and right edges of the sample stage directed towards the field of view at approximately 45 degrees.

Calibration

The camera black reference was with the lens cap on. The camera white reference was a Polaroid 803 positive with 15 ms exposure. To account for the warm color illumination bias of the floodlamps, the red, green, and blue (RGB) values were offset using the white selection tool in the KS400 software, resulting in corrected RGB values that yielded a white image.

Sample setup and image acquisition

Samples are placed on the stage (normal viewing angle) and under ¼" plate glass to minimize topographical effects. Images of the color-bearing graphical portion are acquired at 15 ms exposure.

Image Analysis

Image analysis is performed in Matlab (v.6.5.1, release 13; Mathworks, Inc) with the Image Processing Toolbox (v4.0). RGB images were converted to hue, saturation, and value (HSV) space using Matlab's hsv2rgb.m command. Choosing a saturation lower limit of 0.05 (0-1 scale) resulted in practical detection of all the colored/inked portions of the graphic. The hue, saturation, and value (i.e. luminosity) densiometric distributions were calculated for the detected regions in each image.

As is stated above, any absorbent personal care product may be placed into the wrapper of the present invention. In one embodiment of the present invention, the absorbent personal care article is a tampon and applicator assembly, generally designated 33 (FIG. 7) which is placed into a wrapper component. The tampon and applicator assembly 33 suitably comprises a vaginal tampon 32 (hereinafter "tampon") and corresponding applicator, generally designated 34, for use in inserting the tampon into a woman's vagina. It is understood, however, that the packaged tampon and applicator assembly described herein is applicable to other types of tampons such as, without limitation, medical tampons, dental tampons, surgical tampons, nasal tampons, and the like.

Figure 7:
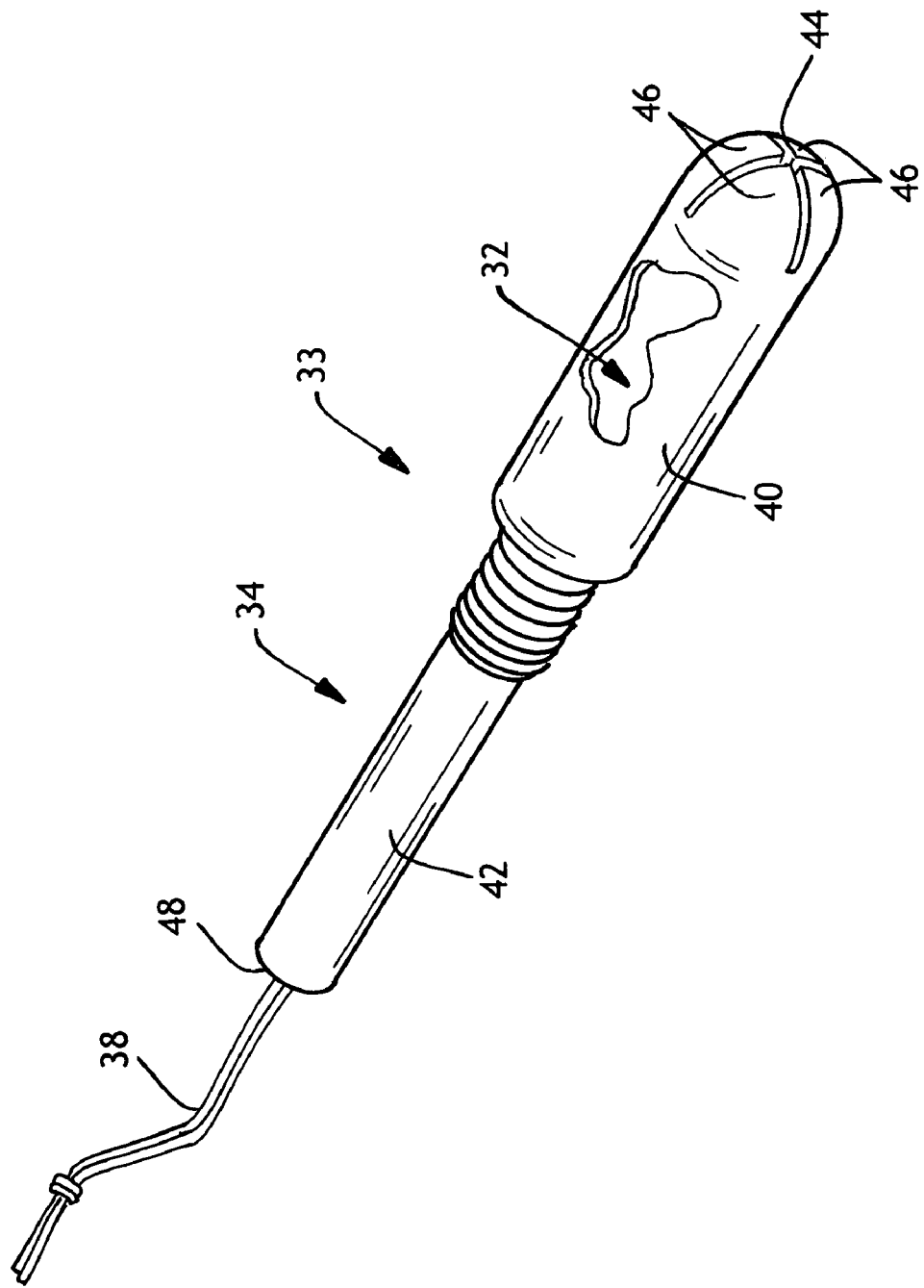
FIG. 7 shows a perspective view of a tampon and applicator assembly, which may be placed into the wrapper component of the present invention.

The tampon 32 illustrated in FIG. 7 has a cylindrical fibrous body that is sized and shaped for insertion into a woman's vagina during her menstrual period to absorb menses, blood, and other body fluid. The tampon 32 includes a withdrawal string 38 that is fastened to the body of the tampon generally adjacent a rearward end thereof. The string 38 is used to pull the tampon 32 from the woman's vagina. The body of the tampon 32 is made of absorbent materials such as absorbent fibers, including natural and synthetic fibers, compressed into a unitary body of a size that may easily be inserted into the vaginal cavity. Suitable fibers include, for example, cellulosic fibers such as cotton and rayon. Fibers may be 100% cotton, 100% rayon, a blend of cotton and rayon, or other materials known to be suitable for tampon use. The body of the tampon 32 has an elongated cylindrical shape so that it has a sufficiently large body of absorbent material to provide the required absorbing capacity. It is understood that the tampon body can be made in a variety of shapes besides cylindrical.

The tampon 32 may also include a cover surrounding the fibrous body. The cover prevents the fibers of the tampon body from directly contacting the inner walls of a woman's vagina. This assures that no fibers will be left behind in the vagina after the tampon 32 is removed. The cover can be tucked into ends of the body of the tampon so as to completely surround and enclose the fibers. The cover can also be constructed from a heat-sealable material to assist in bonding it to the fibers, such as by heat and/or pressure. The cover can be formed from a nonwoven material such as a polyolefin, particularly polypropylene or polyethylene. A suitable material is a spunbond material. Suitable methods and materials for the production of tampons are well known to those skilled in the art.

As illustrated in FIG. 7, the tampon applicator 24, which is used to insert the tampon 32 into a woman's vagina, comprises an outer tube 40 and an inner tube 42. The outer tube 40 is sized and shaped to house the tampon 32. A portion of the outer tube 40 is partially broken away in FIG. 2 to illustrate the tampon 32. In the illustrated embodiment, the outer tube 40 has a substantially smooth exterior surface, which facilitates insertion of the tampon applicator 24, and thus the tampon 32, into a woman's vagina. When the surface of the exterior layer is smooth and/or slippery, the outer tube 40 will easily slide into a woman's vagina without subjecting the internal tissues of the woman's vagina to abrasion. The outer tube 40 may be coated to give it a high slip characteristic. Wax, polyethylene, a combination of wax and polyethylene, cellophane, and clay are representative coatings that can be applied to the exterior layer to facilitate comfortable insertion. The illustrated outer tube 40 is a straight, elongated cylindrical tube. It is understood, however, that the applicator 24 could have different shapes and sizes than those illustrated and described herein.

Extending outwardly from the outer tube is an insertion tip 44. The insertion tip 44, which is formed as one-piece with the outer tube 40, may be dome-shaped to facilitate insertion of the outer tube into a woman's vagina in a comfortable manner. The illustrated insertion tip 44 is made of a thin, flexible material and has a plurality of soft, flexible petals 46 that are arranged to form the dome-shape. The petals 46 are capable of radially flexing (i.e., bending outward) to provide an enlarged opening through which the tampon 32 can exit when it is pushed forward by the inner tube 42. In an alternative configuration, the outer tube may have an abrupt ending without an applicator tip or petals. For example, some cardboard applicators do not have an applicator tip, but may have a film cover or be completely open.

The inner tube 42 is an elongated cylinder that is used to engage the tampon 32 contained in the outer tube 40. A free end 48 of the inner tube 42 is configured for digital manipulation by the user's forefinger so that the user can move the inner tube with respect to the outer tube 40. In other words, the free end 48 functions as a grip for the forefinger of the user. It is also possible to form an enlarged ring or flange on the distal end of the inner tube 42 to provide for a larger contact surface for the user's forefinger.

The inner tube 42 is used to push the tampon 32 out of the outer tube 40 and into the woman's vagina by telescopically moving into the outer tube. As the inner tube 42 is pushed into the outer tube 40 by the user, the tampon 32 is forced forward against the insertion tip 44. The contact by the tampon 32 causes the petals 46 of the insertion tip 44 to radially open to a diameter sufficient to allow the tampon to exit the outer tube 40 and into the woman's vagina. With the tampon 32 properly positioned in the woman's vagina, the tampon applicator 24 is withdrawn. In a used configuration of the tampon applicator 24, the inner tube 42 is received in the outer tube 40. As a result, the used configuration of the tampon applicator 24 has a length that is substantially equal to a length of the outer tube 40.

The inner tube 42, the outer tube 40, and the insertion tip 44 can be formed from any suitable material including, but not limited to, paper, paperboard, cardboard, plastic, thermoplastic film, or a combination thereof. If paper, paperboard, or cardboard is used, it can be coated with a wax or water-insoluble polymer to render it water-resistant. Suitable plastic materials include polyolefins, such as low density polyethylene and low density polypropylene. Construction and operation of the tampon and tampon applicator described heretofore is conventional and known to those skilled in the art. For example, such a tampon and tampon applicator are available from Kimberly-Clark Worldwide Inc. under the tradename KOTEX™ Security.

As is shown in FIGS. 1 and 2, when the absorbent personal care article is a tampon and an applicator, it is desirable that the tampon and applicator are positioned in the wrapper such that the inner tube is closest to the opening device. This allows the tampon and applicator to be removed from the wrapper component by the user without the users touching the outer tube, which could possibly cause contamination of the outer tube prior to insertion into the user's vagina. It is noted, however, that the applicator could in fact be placed into the wrapper with the outer tube being closest to the opening device. The latter is not a preferred configuration to place the tampon applicator into the wrapper.

To open the wrapper of the present invention, the tabs 61, 62 of the opening device are pulled apart in opposite directions. When pulled apart, the rupturable seals are caused to open, revealing the absorbent personal care product contained within the interior space of the wrapper. At this point, the user may remove the absorbent personal care product from the wrapper, and place a used product or, in the case of tampons, the used applicator into the wrapper for disposal.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A packaged absorbent personal care product comprising:
   an absorbent personal care product; and
   a wrapper comprising a front panel and a back panel, each panel having a first longitudinal end, a second longitudinal end, a first side edge and a second side edge; the front panel is joined to the back panel by two longitudinal seals and a lateral seal in a manner to create an interior space adapted to receive and sealingly enclose the personal care product, wherein the lateral seal is located along a line which is substantially parallel with the first longitudinal end and each longitudinal seal has a beginning located one of at or near the lateral seal and an ending located one of at or near the second longitudinal end, each longitudinal seal is located along a line which is substantially parallel with the first and second longitudinal side edges; and wherein the longitudinal seals that is substantially parallel with the first longitudinal side edge comprises a gradient seal strength, and wherein said longitudinal seal comprising a gradient seal strength comprises three to twelve adjacent seal sections extending from the beginning of said longitudinal seal line comprising a gradient seal strength to the end of the longitudinal seal line comprising a gradient seal strength, each seal section in the series of adjacent seal sections has a seal strength which is greater than a previous seal section in the series of adjacent seals.

2. The packaged absorbent personal care product of claim 1, wherein the wrapper further comprises an opening device located at either one of the first longitudinal end or along the first side edge, said opening device comprising a first tab and a second tab, wherein the first tab extends from the front panel and the second tab extends from the back panel.

3. The packaged absorbent personal care product according to claim 2, wherein each of the first and second tabs are located at the first longitudinal end of the front panel and back panel.

4. The packaged absorbent personal care product according to claim 3, wherein the first tab of the front panel is offset from the second tab on the back panel.

5. The packaged absorbent personal care product of claim 2, wherein the tabs are provided with a sensory cue to distinguish the tabs from the front panel and back panel of the wrapper.

6. The packaged absorbent personal care product according to claim 5, wherein the sensory cue comprises a tactile cue.

7. The packaged absorbent personal care product according to claim 6, wherein the tactile cue is one of tabs having a thickness which is greater than the thickness of the front panel and back panel, tabs having a different texture from the front panel and back panel, tabs having one of a scalloped or shaped end portion, or any combination thereof.

8. The packaged absorbent personal care product according to claim 5, wherein the sensory cue comprises a visual cue.

9. The packaged absorbent personal care product according to claim 8, wherein the visual cue is one of tabs having a different color from the front panel and back panel, tabs having a color pattern thereon which is different from a color pattern on the front panel and back panel, and tabs having a solid color and the front panel and back panel having a color pattern.

10. The packaged absorbent personal care product of claim 1, wherein each of the lateral and longitudinal seals comprises one of an adhesive seal, an embossed seal and a combination of an adhesive and embossed seal.

11. The packaged absorbent personal care product of claim 1, wherein both longitudinal side seals have a gradient seal strength.

12. The packaged absorbent personal care product of claim 11, wherein the gradient seal strength increases substantially continuously from the beginning of each longitudinal seal to the end of the longitudinal seal.

13. The packaged absorbent personal care product of claim 12, wherein each longitudinal seal comprises an adhesive seal.

14. The packaged absorbent personal care product of claim 1, wherein the absorbent personal care product comprises one of a tampon, a tampon and applicator, a liner, a pad, an interlabial pad, a bandage or any combination thereof.

15. The packaged absorbent personal care product of claim 1, wherein the absorbent personal care product comprises a tampon and applicator combination.

16. The packaged absorbent personal care product of claim 1, further comprising a second lateral seal, wherein the second lateral seal is one of at or near the second longitudinal end and is substantially parallel with the second longitudinal end.

* * * * *